US00PP13547P3

(12) United States Plant Patent
Crowther et al.

(10) Patent No.: US PP13,547 P3
(45) Date of Patent: Feb. 4, 2003

(54) LYSIMACHIA PLANT NAMED 'WALGOLDALEX'

(75) Inventors: Albert Timothy Alan Crowther, Arundel (GB); David Ralph Tristram, Arundel (GB)

(73) Assignee: David Tristram, Arundel (GB)

( * ) Notice: Subject to any disclaimer, the term of this patent is extended or adjusted under 35 U.S.C. 154(b) by 11 days.

(21) Appl. No.: 09/834,868

(22) Filed: Apr. 14, 2001

(65) Prior Publication Data

US 2002/0152526 P1 Oct. 17, 2002

(51) Int. Cl.[7] ..... A01H 5/00

(52) U.S. Cl. ..... Plt./263

(58) Field of Search ..... Plt./263

*Primary Examiner*—Kent L. Bell

(74) *Attorney, Agent, or Firm*—Mark P. Bourgeois

(57) ABSTRACT

A new cultivar of *Lysimachia punctata* named 'Walgoldalex' that is characterized by it's variegated foliage with green centers and gold margins and leaves that exhibit less distortion than 'Alexander'.

1 Drawing Sheet

Botanical classification: *Lysimachia punctata.*
Variety denomination: 'WALGOLDALEX'.

BACKGROUND OF THE INVENTION

The present invention relates to a new and distinct cultivar of *Lysimachia punctata* and will be referred to hereafter as 'Walgoldalex'. *Lysimachia punctata* is a hardy perennial grown for landscape use.

The new Lysimachia, 'Walgoldalex' was discovered in the summer of 1998 by the inventors in a cultivated area at Walberton Nursery, Arundel, W. Sussex, England. 'Walgoldalex' was discovered as a naturally occurring golden variegated leaf sport arising from *Lysimachia punctata* 'Alexander' (U.S. Plant Pat. No. 10,598).

The new variety of Lysimachia can be characterized by its gold-margined variegation. The parent plant, 'Alexander', has margins that are creamy white in color, as opposed to the gold colored margins of 'Walgoldalex'. The new cultivar is also unique in that the foliage has less distortion to the leaves, a characteristic often exhibited by 'Alexander'. 'Walgoldalex' is similar to 'Alexander' in all other aspects such as plant habit, growth rate, and flowering characteristics. 'Walgoldalex' is unlike any other *Lysimachia punctata*, a species that is not naturally variegated and 'Alexander' is the only other variegated cultivar that is known to the inventors.

Asexual reproduction of the new cultivar was first accomplished by cuttings in Arundel, W. Sussex, England by the inventors in the spring of 1999. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar as a new and unique cultivar of Lysimachia. 'Walgoldalex' has not been tested under all possible conditions and phenotypic differences may be observed with variations in environmental, climatic, and cultural conditions:

1. The foliage of 'Walgoldalex' is variegated with green centers and gold margins.
2. The leaves of 'Walgoldalex' are less distorted during growth in comparison to the leaves of 'Alexander'.
3. The flowers of 'Walgoldalex' are yellow and flowering occurs throughout the summer.
4. 'Walgoldalex' is hardy, a vigorous grower and adaptable to a wide range of cultural conditions.

BRIEF DESCRIPTION OF THE DRAWING

The photograph is of a mature plant of 'Walgoldalex'. The golden variegated foliage as well as the overall habit is illustrated. The colors in the photograph are as accurate as possible by conventional photography.

BOTANICAL DESCRIPTION OF THE PLANT

The following is a detailed description of the new cultivar. Data was collected in August 2000 of a one-year old plant, grown out of doors, in the ground, in Arundal W. Sussex, England. The color determination is in accordance with the 1950 edition of The R.H.S. Colour Chart of The Royal Horticultural Society, London, England, except where general color terms of ordinary dictionary significance are used.

Botanical classification: *Lysimachia punctata* 'Walgoldalex'.

Commercial classification: Hardy Perennial for landscape use.

Parentage: Naturally occurring sport of *Lysimachia punctata* 'Alexander'.

General description:

*Blooming period.*—Blooms from late June–August in temperate climates.

*Plant habit.*—Upright, moderately branched, more clump-forming than the species.

*Height and spread.*—30–75 cm in height, 30–60 cm (eventually more) in width.

*Hardiness.*—Zone 4–8.

*Type.*—Hardy herbaceous perennial.

*Root system.*—Fleshy, branched, slightly stoloniferous.

*Propagation.*—Terminal tip cuttings.

*Time to initiate roots.*—About 10 days at 20° C.

*Time to develop roots.*—About 14 days at 20° C.

*Culture.*—Fertile, moisture retentive soils in full sun or part shade.

*Diseases and pests.*—No sensitivity or resistance observed.

Stems:

*Shape.*—Round.

*Size.*—1.3–6 mm in diameter.

*Surface.*—Pubescent, longitudinal ridges.

*Color.*—138A.

*Color of stem ridges.*—138C.

*Branching.*—Up to 10 lateral branches/stem.

*Internode length.*—1 to 4 cm.

Foliage:

*Shape.*—Ovate.

*Apex.*—Acute.

*Base.*—Obtuse to cuneate.

*Venation.*—Upper side: recessed, especially the midvein. Lower side: prominent.

*Margins.*—Entire, very finely toothed.

*Arrangement.*—Opposite, occasionally alternate.

*Quantity.*—Up to 30 per lateral branch.

*Surface.*—Pubescent.

*Length.*—Up to 10 cm.

*Width.*—Up to 5.0 cm.

*Petiole.*—Length: 3–6 mm. Width: 3 mm (incl. wings). Depth: 1.5 mm. Color: 138A. Color of wings: 162B.

*Color.*—Young: Upper: Center: 144A. Intermediate: 138D. Margin: 162B. Lower: Center: 144B. Intermediate: 138D. Margin: 162B. Mature: Upper: Center: 146B to 191B. Intermediate: 195B. Margin: 161B to 161C. Lower: Center: 146C to 191C. Intermediate: 195B. Margin: 161C.

Flowers:

*Type.*—Single, bell-shaped, flaring from the base, arranged on spikes arising from leaf Axils, flowers face outward from all sides of the flower stem.

*Fragrance.*—None.

*Lastingness* (*on plant*).—Up to 7 days, self cleaning and not persistent.

*Quantity.*—20 to 30 flowers per spike, typically 3–10 flowers are open at one time.

*Width.*—2.5 cm.

*Height.*—1.3–1.9 cm.

*Peduncle.*—Attachment: Held at a 30° angle to stem. Length: 1.25–5 cm. Width: 3 mm. Color: 138A to 138C (range).

*Petal.*—Number 5. Shape: ovate. Appearance: dull with faint reddish longitudinal veining. Apex: acute. Margins: ciliate. Length: 1.3–1.9 cm. Width: 1 cm. Color (opening and fully open): Upper surface: 12A to 14B (range) with 182A on the base. Lower surface 12A.

*Calyx.*—Sepals: Number 5. Shape: linear to lanceolate. Apex: acute. Surface: rough, pubescent. Length: 3–5 mm. Width: 3 mm. Color: Upper surface: Center: 144A. Margin: 162B. Lower surface: Center: 144A. Margin: 162B.

*Flower bud.*—Length: about 1.2 cm. Width: about 3 mm. Color: 12A.

Reproductive organs:

*Stamens.*—Number: 5. Anthers: Length: about 1.5 mm. Width: about 0.75 mm. Pollen: Color: 21A. Abundance: moderate.

*Pistil.*—Number: 1. Length: 3–5 mm. Stigma: Color: 139B. Style: Color: 194B. Length 3–5 mm.

*Ovary.*—Number: 1. Color: varies between 194A and 196D.

Fruit/seed:

*Fruit.*—Occurrence: Low. Shape: 5 valved capsule.

*Seed.*—Size: 0.15 mm in diameter. Color: 165A in color.

We claim:

1. A new and distinct cultivar of Lysimachia plant named 'Walgoldalex' as described and illustrated.

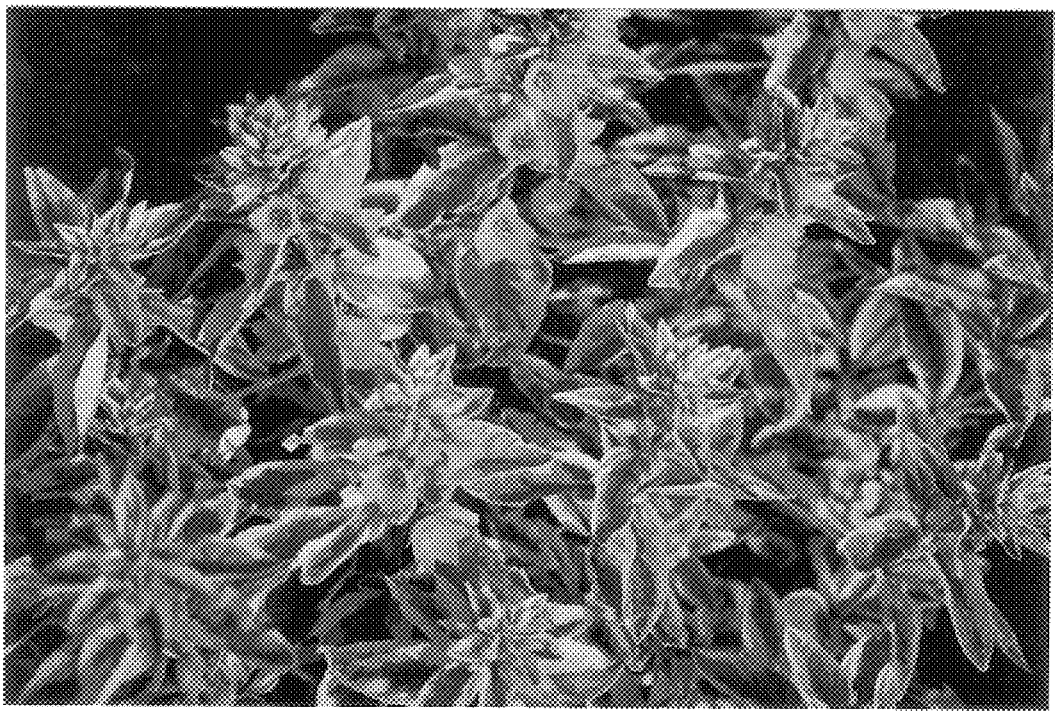

* * * * *